United States Patent
Mukhopadhyay (10) Patent No.: US 11,421,201 B2
(45) Date of Patent: Aug. 23, 2022

(54) BIOMASS WITH BIOENGINEERED YEAST, ASSOCIATED ORGANIC COMPOUNDS, AND RELATED METHODS

(71) Applicant: Tekkware., Inc., South Bend, IN (US)

(72) Inventor: Abhijit Mukhopadhyay, West Lafayette, IN (US)

(*) Notice: Subject to any disclaimer, the term of this patent is extended or adjusted under 35 U.S.C. 154(b) by 0 days.

(21) Appl. No.: 16/282,673

(22) Filed: Feb. 22, 2019

(65) Prior Publication Data
US 2019/0185810 A1 Jun. 20, 2019

Related U.S. Application Data

(63) Continuation-in-part of application No. 15/697,446, filed on Sep. 7, 2017, now abandoned.

(60) Provisional application No. 62/384,616, filed on Sep. 7, 2016.

(51) Int. Cl.
| | | |
|---|---|---|
| C12N 1/32 | (2006.01) | |
| C12N 9/42 | (2006.01) | |
| C12N 1/16 | (2006.01) | |
| C12P 7/56 | (2006.01) | |
| C12P 7/10 | (2006.01) | |
| C12P 21/00 | (2006.01) | |
| C12P 7/06 | (2006.01) | |

(52) U.S. Cl.
CPC ............ *C12N 1/32* (2013.01); *C12N 1/16* (2013.01); *C12N 9/2437* (2013.01); *C12N 9/2445* (2013.01); *C12P 7/10* (2013.01); *C12P 7/56* (2013.01); *C12P 21/00* (2013.01); *C12Y 302/01004* (2013.01); *C12Y 302/01021* (2013.01); *C12Y 302/01091* (2013.01); *C12P 7/06* (2013.01); *C12P 2203/00* (2013.01); *Y02E 50/10* (2013.01)

(58) Field of Classification Search
CPC .......... C12N 1/32; C12N 1/16; C12N 9/2437; C12N 9/2445; C12P 7/10; C12P 7/56; C12P 21/00; C12P 7/06; C12P 2203/00; C12Y 302/01004; C12Y 302/01021; C12Y 302/01091
See application file for complete search history.

(56) References Cited

U.S. PATENT DOCUMENTS

2018/0245034 A1   8/2018   Mukhopadhyay

OTHER PUBLICATIONS

Ishola et al. Simultaneous saccharification, filtration and fermentation (SSFF): A novel method for bioethanol production from lignocellulosic biomass. Bioresource Technology, vol. 133, Apr. 2013, pp. 68-73.*
Ishida et al. Efficient Production of L-Lactic Acid by Metabolically Engineered *Saccharomyces cerevisiae* with a Genome-Integrated L-Lactate Dehydrogenase Gene, Appl and Environ Microbiol (2005), 71(4): 1964-190.*
Tang et al. High β-Glucosidase Secretion in *Saccharomyces cerevisiae* Improves the Efficiency of Cellulase Hydrolysis and Ethanol Production in Simultaneous Saccharification and Fermentation. J. Microbiol. Biotechnol. (2013), 23(11): 1577-1585.*
International Searching Authority At the European Patent Office, International Search Report and Written Opinion for International Application No. PCT/US2019/020897, dated May 22, 2019, 12 pages.
Bera, et al., A genetic overhaul of *Saccharomyces cerevisiae* 424A (LNH-ST) to improve xylose fermentation, Journal of Industrial Microbiology & Biotechnology, May 1, 2011, pp. 1367-5435, vol. 38, No. 5.
Doran-Peterson, et al., Microbial conversion of sugars from plant biomass to lactic acid of ethanol, The Plant Journal, Jan. 1, 2008, pp. 582-589, vol. 54.

* cited by examiner

*Primary Examiner* — Iqbal H Chowdhury
(74) *Attorney, Agent, or Firm* — Louis Wu

(57) ABSTRACT

Provided are various genetically engineered strains of TEKK microorganisms, e.g., yeast in a container of industrial-scale volume containing biomass, wherein the microorganisms are capable of fermenting C5 material to produce desirable organic compounds. Also provided are methods for efficiently producing industrial-scale volumes of the desirable organic compounds, e.g., lactic acid, by TEKK strains of microorganisms such as TEKK-LAC and variants thereof.

16 Claims, 5 Drawing Sheets

FIG. 1 pTEKK-LAC

FIG. 2 pYKDR-TEKK-LAC

FIG. 3

FIG 4. Fermentation of glucose to lactic acid and ethanol by *S cerevisiae* TEKK-LAC FIG. 5. Conversion of glucose to lactic acid by TEKK-LAC EtOH⁻ with no pH adjustment FIG. 6. Conversion of glucose to lactic acid by TEKK-LAC EtOH⁻ with pH adjustment FIG. 7. Conversion of xylose to lactic acid by 424A(LNH-ST)/pYKDR-TEKK-LAC FIG. 8. Co-fermentation of C6/C5 to lactic acid by 424A(LNH-ST)/pYKDR-TEKK-LAC FIG 9. Lactic acid production by *S cerevisiae* 424A(LNH-ST)/pYKDR-TEKK-LAC from corn stover hydrolysate

BIOMASS WITH BIOENGINEERED YEAST, ASSOCIATED ORGANIC COMPOUNDS, AND RELATED METHODS

CROSS REFERENCE TO RELATED APPLICATIONS

This patent application is a continuation-in-part of U.S. Utility patent application Ser. No. 15/697,446 entitled "BIOMASS WITH BIOENGINEERED MICROORGANISM SUCH AS YEAST, ASSOCIATED ORGANIC COMPOUNDS, AND RELATED METHODS," filed Sep. 7, 2017, which claims priority to U.S. Provisional Patent Application Ser. No. 62/384,616 entitled "BIOMASS WITH BIOENGINEERED MICROORGANISM SUCH AS YEAST, ASSOCIATED ORGANIC COMPOUNDS, AND RELATED METHODS," filed Sep. 7, 2016, and is related to U.S. Patent Application Ser. No. 62/045,454, entitled "XYLOSE AND GLUCOSE CO-FERMENTING MICROORGANISM THAT EXPRESSES ACTIVE GLUCOAMYLASE," filed Sep. 3, 2014, and is also related to U.S. patent application Ser. No. 14/839,372, entitled "XYLOSE AND GLUCOSE CO-FERMENTING MICROORGANISM THAT EXPRESSES ACTIVE GLUCOAMYLASE," filed Aug. 28, 2015 by applicant Tekkware, Inc., the disclosures of which are incorporated by reference in their entireties.

BACKGROUND

Technical Field

In general, the invention relates to microorganisms that have industrial applicability and usefulness in contexts such as those involving organic industrial chemicals and/or those implicating biofuel production. More particularly, the invention relates to bioengineered microorganisms such as engineered yeasts, organic compounds associated therewith such as lactic acid, and methods for carrying out the inventive subject matter associated with any of the foregoing.

Description of Background Art

In response to sharp increase in crude oil prices over the last two decades as well as the reality of dwindling world's oil reserves, there exists a growing need to reduce the dependency on fossil fuels and explore large-scale production of chemicals via fermentation of sugars from renewable resources. Plastics derived from petrochemicals have become indispensable materials in our daily life. Furthermore, most of these materials are not biodegradable and are contributing to an ever-growing disposal and pollution problems for the world. Metabolic engineering is well positioned to develop new and improved microorganisms to solve and/or reduce such problems by enabling the low-cost production of biological polymers and polymer precursors. These biodegradable polymer materials may replace plastics derived from petrochemicals and address global problems in fossil fuel dependency and environmental management.

Lactic acid is an important chemical that can be efficiently converted to propylene glycol, acrylic polymers, and polyesters. Lactate esters derived from biologically produced lactic acid (biolactic acid) are now considered as alternative benign solvents. Lactic acid is also a raw material for production of biodegradable poly(lactic acid), which is in growing demand to be used for the synthesis of biodegradable polymers.

Lactic acid can be produced by certain microorganisms during fermentation. The traditional important industrial microorganisms for the production of lactic acid belong to the genera of *Lactobacillus, Bacillus*, and *Rhizopus*. However, during a typical lactic acid fermentation, the low pH (due to lactic acid production) has an inhibitory effect on the metabolic activity of these cell cultures. In addition, levels of free acid at or above 1-2 wt % of total combined lactic acid are considered toxic to cells in these cultural systems. The addition of $Ca(OH)_2$, $CaCO_3$, NaOH, or $NH_4OH$ to neutralize the lactic acid is a conventional operation to minimize the negative effect of pH and to un-dissociate lactic acid accumulation in industrial processes. However, the neutralization process results in co-producing large amount of unwanted byproduct such as calcium sulfate (gypsum), which has created a serious environment problem.

Thus, there is a critical need for the development of improved microbial processes for the production of lactic acid at lower pH from renewable resources to meet the commercial demand.

An alternative method to produce lactate is to develop a fermentation process with microorganisms thrive and are metabolically active at much lower pH values. Yeast such as *Saccharomyces cerevisiae* are tolerant of lower pH levels than the traditional microorganisms used for lactic acid production. Furthermore, this yeast also benefits from having the 'GRAS' (generally regarded as safe) statutes and can be even used for food and pharmaceutical production.

Lactic acid is traditionally produced by fermenting glucose or other hexose sugars from feedstocks such as cornstarch or cane sugar. These feedstocks are in limited supply. However, theoretically, lactic acid should also be able to be produced from sugars recovered from plant cellulosic biomass (corn stover, rice straw, wood, grasses, waste papers, etc.), which is not only renewable and available domestically, but also available at a low cost and in great abundance.

Thus, certain widely available plant biomass is an attractive feedstock for ethanol production by fermentation because it is renewable, and available at low cost and in large amounts around the world. The major fermentable carbohydrate sugars from cellulosic materials are six-carbon (C6) sugars such as glucose and five-carbon (C5) sugars such as xylose. Glucose and xylose are major sugars present in all types of cellulosic biomass (wood chips, weed grasses, straws, corn stover, potatoes, brown rice, etc.) with varying ratio of glucose to xylose being approximately 2 to 1. The most desirable fermentations of cellulosic materials would, of course, completely convert both C5 and C6 sugars to ethanol.

For example, glucose-fermenting yeasts such as *Saccharomyces* yeast like *Saccharomyces cerevisiae* had been thought to be unable to use xylose both for growth and fermentation. However, a number of researchers have demonstrated that it is possible to genetically engineer naturally-occurring yeasts to do so by introducing exogenous genetic materials through known techniques such as those described in U.S. Pat. Nos. 5,789,210, 7,527,927 and 8,652,772, each to Ho et al. See also, Sedlak et al. (2004), "Production of Ethanol from Cellulosic Biomass Hydrolysates Using Genetically Engineered *Saccharomyces* Yeast Capable of Cofermenting Glucose and Xylose," APPLIED BIOCHEMISTRY AND BIOTECHNOLOGY, 113-116:403-16. U.S. Pat. Nos. 5,789, 210, 7,527,927 and 8,652,772, each to Ho et al. Sedlak et al. (2004), "Production of Ethanol from Cellulosic Biomass Hydrolysates Using Genetically Engineered *Saccharomyces*

Yeast Capable of Cofermenting Glucose and Xylose," APPLIED BIOCHEMISTRY AND BIOTECHNOLOGY, 113-116:403-16.

Similarly, different strains of yeast may also be sexually bred and/or asexually selected in specific culture media at controlled temperatures to optimize their functionality in industrial fermentation processes. Additional background art pertaining to the invention described below include, for example, US Patent Application No. 20160060659 to Ho.

As commercialization of biotechnology using human-engineered and/or selectively reproduced yeasts have progressed, certain strains and variants thereof are becoming increasingly valuable. Such strains may, for example, be effectively designed for optimized expression of commercially valuable biochemicals such as lactic acid. In turn, such biochemicals may be used to solve societal, economic and/or industrial problems and/or bottlenecks that are occurring now or that may turn up in the future.

Thus, the invention described herein pertains to such human-engineered, selectively bred and/or functionally optimized organisms such as yeasts to address such problems and/or bottlenecks in the implementation of biotechnology in a post-bench top and relatively large-scale processes so as to facilitate rate and quality of progress for various useful biotechnological arts.

SUMMARY

Provided are various strains of useful, novel and nonobvious microorganisms identifiable by the term "TEKK," samples of which are available from Tekkware, Inc. (a Delaware corporation with offices in Indiana and Massachusetts).

In a first embodiment, a container of industrial-scale volume, e.g., a reaction tank, containing biomass is provided with microorganisms capable of fermenting C5 material. The yeast is also capable of expressing and/or secreting β-glucosidase having nonnegligible enzymatic activity for breaking down the biomass. The yeast is TEKK-β-glucosidase, TEKK-endocellulase TEKK-exocellulase, or a variant thereof. The container may be reaction tank.

In some embodiments, the yeast is hardened, e.g., for C5 material. The yeast may also be capable of fermenting C6 material as well as hardened for C6 material.

Also provided are methods for producing a desired biochemical, e.g., β-glucosidase, endocellulase, exocellulase, ethanol, and/or lactic acid, in an industrial scale volume. The methods include at least steps (a) and (b) which may be carried out separately, together, in any order effective to produce the desired biochemical. Step (a) involves putting together in a container of industrial-scale volume biomass of an industrial-scale volume of biomass, water, and a TEKK yeast or a yeast traceable to a TEKK yeast. Step (b) involves bringing the container to a temperature suitable for the TEKK yeast to produce the desired biochemical in an industrial-scale volume. Optionally, the desired biochemical is isolated from a byproduct that may be undesired and/or also desirable.

Further provided are efficient lactic acid generating microorganisms and variations thereof, e.g., collectively designated as TEKK-LAC.

Additional embodiments, features and advantages of the invention will be apparent from the following description.

BRIEF DESCRIPTION OF THE DRAWINGS

Additional graphs pertaining to experimental data associated from TEKK strains of microorganisms are available from Tekkware, Inc. (South Bend, Ind.) upon request.

DETAILED DESCRIPTION

Definitions and Overview

Before describing the present invention in detail, it should be noted that embodiments of the invention may take the form of a useful process, machine, manufacture, or composition of matter, or any new and useful improvement thereof. It is also to be understood that the invention is not limited to specific species of microorganisms, or whether the invention takes the form of an organism that is classified as fungal, bacterial, or otherwise, as such may vary. It is further to be understood that the terminology used herein is for the purpose of describing particular embodiments only, and is not intended to be limiting.

In addition, as used in this specification and the appended claims, the singular article forms "a," "an," and "the" include both singular and plural referents unless the context clearly dictates otherwise. Thus, for example, reference to "a single-celled microorganism" includes a plurality of singled-celled microorganisms as well as one single-celled microorganism, reference to "a gene" includes a single gene as well as a combination of genes, and the like.

In this specification and in the claims that follow, reference is made to a number of terms that shall be defined to have the following meanings, unless the context in which they are employed clearly indicates otherwise:

The terms "active," and "activity" are used in their ordinary sense to refer to a state characterized by action rather than inertness.

The term "amylase" is used in its ordinary sense to refer to an enzyme that catalyzes the hydrolysis of starch into sugars. For example, the term "glucoamylase" refers to an enzyme that catalyzes the hydrolysis of glucosic material into glucosic sugars.

The term "alcohol" is used in its ordinary sense to refer to any of a class of chemical compounds having the general formula ROH, where R may represent an alkyl group and —OH, a hydroxyl group, as in ethanol, $C_2H_5OH$. Additional examples of alcohols include xylitol, glycerol and other sugar alcohols or polyols.

The terms "bioengineer," "bioengineering," and the like are used herein in their ordinary biochemical sense in a microcellular context and refer to techniques that may be carried out to achieve an intended result. For example, bioengineering may involve using plasmids, viruses, or other vectors to introduce genetic material into DNA of a living organism. In addition or in the alternative, bioengineering may involve the use of techniques such sexual breeding, asexual selection, and/or gene editing using techniques such as CRISPR (Clustered Regularly Interspaced Short Palindromic Repeats) to effect the intended result.

The term "biomarker" is used herein to refer to nucleotidic material such as DNA or RNA that may serve as an identifier of strains of the inventive microorganism. For example, a biomarker of a particular strain of the inventive microorganism may be at least about 90% identical to a variant of the same strain of microorganism.

The term "biomass" is used in its ordinary sense and refers to organic matter, especially plant matter, which is therefore regarded as a potential energy source for reactions that produce desired organic chemical compounds such as lactic acid. The term "biomass" includes unprocessed as well as processed organic matter that may or may not originate from plants such as starches and celluloses. Exemplary biomass composition may include one or more of the following: corn stover, rice straw, wood, grasses, waste papers, etc. Biomass may also refer to compositions of matters including components of organic matter such as sugars, oligomers, polymers, etc. thereof, e.g., in combination with yeast. Thus, a culture of a yeast in combination with nutrients that sustain the yeast is considered a form of biomass.

The terms "C5" and "C6" are used herein to refer to sugars, oligomers thereof and polymers of any of the foregoing that contain particular rings structures of particular shapes and geometries under certain pH, temperature, pressure, and other fermentation conditions. For example, "C5" compounds are generally considered pentosic in nature. A non-limiting example of a C5 compound is xylose that has been isolated from wood. Similarly, arabinose is also generally considered a C5 compound. In contrast, "C6" compounds are general hexosic in nature. A non-limiting example of a C6 compound is glucose that is stored as a polymer, in plants as starch and in animals as glycogen, for times of need.

The term "cellulase" is used in its ordinary sense and refers to a catalyst that may be used to cleave cellulose. For example, there are five general types of cellulases based on the type of reaction catalyzed.

"Cellobiases" or beta-glucosidases hydrolyse the exocellulase product into individual monosaccharides. For example, oxidative cellulases depolymerize cellulose by radical reactions, as for instance cellobiose dehydrogenase (acceptor). Cellulose phosphorylases depolymerize cellulose using phosphates instead of water. Similarly, avicelase has almost exclusively exocellulase activity, since avicel is a highly micro-crystalline substrate.

Within the above types there are also progressive (also known as processive) and nonprogressive types. Progressive cellulase will continue to interact with a single polysaccharide strand, nonprogressive cellulase will interact once then disengage and engage another polysaccharide strand.

"Endocellulases" randomly cleave internal bonds at amorphous sites that create new chain ends.

"Exocellulases" or "cellobiohydrolases" cleave two to four units from the ends of the exposed chains produced by endocellulase, resulting in tetrasaccharides or disaccharides, such as cellobiose. Exocellulases are further classified into type I, that work processively from the reducing end of the cellulose chain, and type II, that work processively from the nonreducing end.

Cellulase action is considered to be synergistic as all classes of cellulase can yield much more sugar than any one individually. Aside from ruminants, most animals (including humans) do not produce cellulase in their bodies and can only partially break down cellulose through fermentation, limiting their ability to use energy in fibrous plant material.

The term "cellulose" is used in its ordinary sense and refers to an organic compound with the general formula $(C_6H_{10}O_5)_n$, a polysaccharide consisting of a linear chain of several hundred to many thousands of $\beta(1\rightarrow 4)$ linked D-glucose units. Cellulose is an important structural component of the primary cell wall of green plants, many forms of algae and the oomycetes.

Similarly, the term "hemicellulose" also known as polyose) is used to describe any of several heteropolymers (matrix polysaccharides), such as arabinoxylans, present along with cellulose in almost all plant cell walls.

The term "coproduct" is used in its ordinary sense and refers to an incidental product, e.g., something produced during the manufacture or production of something else, often something useful or commercially valuable.

The term "culture" is used in its ordinary biological sense and refers to the cultivation of live material, e.g., yeast, in an artificial or natural medium that contains nutrients, e.g., a corn stover suspension or solution.

The term "domesticated" as used herein refers to plants that are generally cultivated for food or otherwise naturalized for crops. Examples of domesticated plants include, corn, potatoes, rice, etc.

The terms "efficient," "efficiently" and the like are used in their ordinary sense and are used to describe biological and/or chemical means that achieve improved productivity with minimum wasted time, effort, and/or expense, e.g., via. enhanced performance in terms of yield, yield rate, throughput, absence of wanted side reactions, and the like. For example, an efficient biochemical process carried out with the invention effects greater productivity relative to a comparable biochemical process that is less efficient inefficient in nature. The term is to be interpreted in context in a manner such that the claims encompass only validly patentable subject matter given the unpredictability nature of art relevant to the present invention.

The term "enzyme" is used to refer to any of various proteins, as pepsin, originating from living cells and capable of producing certain chemical changes in organic substances by catalytic action, as in digestion.

For example, for long term storage, most living organisms of the invention should be kept at ultralow temperatures below about −70 or about −80° C. In preparation for fermentation use, the inventive yeasts cultures should be thawed to a temperature of about 0° C. to about 70° C. More specifically, a fermentation temperature range of about 25° C. to about 35° C. is typically preferred. Optimally, a temperature range of about 28° C. to about 32° C., optimally about 30° C., may be used, keeping mind that a certain amount of deviation may be permitted. In any case, specific fermentation temperatures and ranges thereof may vary depending on the requirements associated with efficient commercial production, e.g., of ethanol and/or other organic compounds of interest. For example, certain processes may involve different temperature profiles over time, so as to ensure appropriate production of glucoamylase and other enzymes without contributing to microorganism health problems associated with temperature and unwanted byproducts.

The terms "gene," "genetic material," and the like are used to refer a molecular unit of heredity of a living organism. The terms are typically used to identify some stretches of DNA or RNA that code for a peptidic material such as an enzyme.

The terms "glucose," "glucosic," "glucosidic," "C6," and the like are used in their ordinary biochemical sense and refer to a sugar, $C_6H_{12}O_6$, having several optically different forms, the common dextrorotatory form (dextroglucose, or -glucose) occurring in many fruits, animal tissues and fluids, etc. Exemplary glucosic materials include levoglucose, dextrose, maltose, sucrose, starches, and starch syrups such as corn syrup.

The terms "harden," "hardened" and the like are used in an industrial sense and refer to microorganisms that are relatively stable for their intended use. Hardening typically involves replicating the microorganisms numerous times to make sure that the microorganisms will not lose properties needed to carry out their intended function.

The term "industrial" as in "industrial scale" is used in its ordinary economic sense and refers to the production of goods or co-products that makes sense within a particular economy. For example, containers for carrying out the invention in an industrial are typically at least 100 gallons in volume. Preferably, the volumes range from about 500 to 2000 gallons. Optimal container volume can be determined upon an analysis of supply and demand issues associated with yeast production and yield.

The prefix "micro" refers to items having dimensions on the order of micrometers or having volumes on the order of microliters or somewhat less in size or dimensions. Thus, for example, the term "microorganism" refers to an organism, comprising a single cell, several cells, tens of cells, or greater than one hundred cells, wherein a representative dimension of the organism is about on the order of microns or submicrons. Such a microorganism, for example, can be a yeast or other fungus. The largest dimension of a microorganism is no greater than about 1 millimeter. Other terms containing the prefix "micro" are to be construed in a similar manner.

Similarly, the prefix "nano" is used in a similar manner as "micro" but refers to items having even smaller dimensions, e.g., on the order of nanometers or having volumes on the order of nanoliters or somewhat less in size or dimensions. Thus, for example, the term "nanocellulose" refers to cellulose, e.g., in particulate form, having a critical volume or dimension on the order of nanoliters or nanometers instead of a critical volume or dimension better described using the "micro" prefix.

The term "nonnegligible" generally refers to something substantial, significant or nontrivial, e.g., something not so small, trifling, or unimportant that it may safely be neglected or disregarded. As used herein, the term should be construed in an economic, industrial, scientific, technological, and/or biological sense.

For example, it is imaginable, though extremely unlikely, a naturally occurring microorganism in the form of a *Saccharomyces* genus yeast may through natural selection without any human intervention be able to coferment glucose and xylose while expressing a nonnegligible amount of glucoamylase. However, such production of glucoamylase does not necessarily result in efficient C5 and C6 cofermentation.

In addition, numerous strains of claimed microorganisms have been tested against other microorganisms in laboratory and/or industrial scale fermentors and have exhibited significant improvement in terms of performance. In any case, the claims below are not intended to cover such a microorganism to an extent that would render the claims invalid under 35 U.S.C. § 101 or related case law in any applicable jurisdiction.

The terms "nucleotide," "nucleotidic," and the like refer to organic molecules that serve as the monomers or subunits of nucleic acids like DNA (deoxyribonucleic acid) and RNA (ribonucleic acid). The building blocks of nucleic acids, nucleotides are composed of a nitrogenous base, a five-carbon sugar (ribose or deoxyribose) and at least one phosphate group.

The prefix "oligo" as in "oligomer" is used in its ordinary sense to refer to a short" polymer that has only a few monomeric units. Thus, an "oligosaccharide" is a polysaccharide with relatively few saccharidic units.

The term "optional" or "optionally" means that the subsequently described circumstance may or may not occur, so that the description includes instances where the circumstance occurs and instances where it does not.

The terms "peptide," "peptidic," and the like refer to a compound containing at least one amino acid, more typically two or more amino acids in which the carboxyl group of one acid is linked to the amino group of the other.

A "plasmid" is a small DNA molecule that is physically separate from, and can replicate independently of, chromosomal DNA within a cell. Commonly found as small circular, double-stranded DNA molecules in microorganisms, plasmids carry genes that may benefit survival of an organism.

The term "potable" is used in its ordinary sense to refer to a fluid that is generally considered safe to drink. In contrast, the term "denatured" refers to a fluid that is generally considered toxic to the drinker.

The term "promoter" may refer to a region of DNA that initiates transcription of a particular gene.

The term "recombinant" is used to refer to matter that is of, relating to, or involved in genetic recombination, particularly by using scientific techniques carried out in vitro.

The term "residue" is used to refer something left over, e.g., something that remains after a process involving the removal of part of the original has been completed.

The terms "saccharide," "saccharidic," and the like are used in their ordinary sense to refer to an organic compound containing a sugar, e.g., a simple sugar such as a monosaccharide or an ester of sucrose, or a polysaccharide like starch.

The term "traceable" as in "a microorganism traceable to a TEKK yeast" (or as in a "variant" of a TEKK yeast) is used in its ordinary legal and/or common-sense context and refers to organic matter whose origins can be attributed in part or in whole to TEKK yeast. For example, progeny of any specific TEKK yeast, regardless whether produced sexually or asexually, as well as microorganisms bioengineered from the TEKK yeast or any component thereof, are considered traceable to the specific TEKK yeast. The term is to be construed broadly and legitimately, e.g., legally effective even if the progeny is 100 to 1000 generations removed from an original parent yeast strain as long as this case is remains valid and enforceable.

The term "variant," when used in connection with a "microorganism," e.g., a baseline yeast strain, refers to a form or version of microorganism that differs in some respect from other forms of the baseline strain microorganism, but not to a degree that would render the variant for the purpose of comparison incompatible from a biochemical standpoint relative to the baseline yeast strain. For example, a baseline yeast strain may differ relative to a variant yeast strain genetically by no more than 10%. That is, the baseline yeast stain may be 90%, 95%, 99%, 99.5%, 99.9 percent generically identical to its variants and be generally considered of the same biological species. In contrast, lactobacillis microorganisms would not generally be considered a variant of yeast organisms, because they are considered different species.

A "vector" is a DNA molecule used in molecular cloning as a vehicle to artificially carry foreign genetic material into another cell, where the genetic sequence of the DNA molecule can be replicated and/or expressed.

The term "xylose," "xylosic," "C5," and the like are generally synonymously used in their ordinary sense to refer to a pentose sugar, $C_5H_{10}O_5$, derived from xylan, straw, corncobs, etc. For example, xylulose is a type of pentose sugar. The term "xylosic" when applied to a molecule does not necessarily exclude glucosic molecules and vice versa. For example, it is theoretically possible for a polysaccharide to have a chain structure that includes monomeric units, some of which being xylosic while others of which being glucosic in structure.

The invention relates to microorganisms as set forth in the claims below that facilitate and/or that are capable of fermenting biomass, e.g., in the form of a fluid such as a liquid and/or solution. Some microorganisms by themselves may be capable of fermenting xylosic material and of expressing and/or secreting glucoamylase having nonnegligible enzymatic activity for breaking down glucosic polysaccharides of the biomass. Typically, but not necessarily, the microorganism has nucleotidic material traceable to a man-made recombinant process. The microorganism may be a yeast, e.g., of the genus *Saccharomyces*, that ferments glucose to ethanol. However, other microorganisms such as those discussed in U.S. Pat. No. 5,789,210 to Ho et al may be used as a starting point to practice in the invention. The microorganism may be in diploid, polyploid, or a haploid state for asexual or sexual reproduction, respectively. *Saccharomyces cerevisiae* represents an exemplary microorganism of the invention.

Ordinarily, the solution is safe to be used as a transportation fuel, perhaps even for human and animal ingestion, e.g., via eating, drinking, inhaling, injection, or some other means.

Recombinant Genes

In general, any of a number of recombinant genes may be used to carry out the invention. While precise gene sequences are not discussed herein in detail, gene sequences associated with the invention is available to the USPTO and other governmental agencies upon request. Samples of materials containing relevant gene sequences are also available on request for a nominal fee.

Exemplary genes associated with xylosic fermentation are discussed in U.S. Pat. No. 5,789,210 to Ho et al. and include XR, XD and XK genes. Such genes are well known to occur in a wide variety of microorganisms and, in fact, as discussed hereinabove, numerous XR, XD and XK genes have been identified and isolated. The particular source of these genes is not critical to the broad aspects of this invention; rather, any nucleotidic encoding peptidic enzymes having xylose reductase activity (the ability to convert D-xylose to xylitol with NADPH or NADH as cofactor), xylitol dehydrogenase activity (the ability to convert xylitol to D-xylulose with NAD+ as cofactor), or xylulokinase activity (the ability to convert D-xylulose to D-xylulose-5-phosphate) will be suitable. These genes may be obtained as naturally-occurring genes, or may be modified, for example, by the addition, substitution or deletion of bases to or of the naturally-occurring gene, so long as the encoded protein still has the enzyme activities encoded by the XR, XD or XK genes. Similarly, the genes or portions thereof may be synthetically produced by known techniques, again so long as the resulting DNA encodes a protein exhibiting the desired xylose reductase, xylitol dehydrogenase, or xylulokinase activity.

As examples, suitable sources of XR and XD genes include xylose-utilizing yeasts such as *Candida shehatae, Pichia stipitis, Pachysolen tannophilus*, suitable sources of XK genes include the above-noted xylose-utilizing yeasts, as well xylose non-utilizing yeasts such as those from the genus *Saccharomyces*, e.g. *Saccharomyces cerevisiae*, the genus *Schizosaccharomyces*, e.g. *Schizosaccharomyces pombe*, and bacteria such as *Escherichia coli, Bacillus species, Streptomyces* species, etc. Genes of interest can be recovered from these sources utilizing conventional methodologies. For example, hybridization, complementation or PCR techniques can be employed for this purpose.

Exemplary Process

In any case, any of a number of known recombinant processes or methods may be used to introduce exogenous genetic material into microorganism of the invention. Such processes are not limited by any particular type of vector, as such may vary. Exemplary suitable processes and methods are discussed in Yocum et al. and Ho et al. Exemplary vector types suitable for use with the invention include plasmid vectors, binary vectors, cloning vectors such as those for integrating genes into a host chromosome, expression vectors, shuttle vectors, and viral vectors. Deletions may be carried out using CRISPR technology should it become necessary to knock out the activity of certain gene sequences.

Thus, microorganisms of the invention may be produced by a process that involves transforming cells of the microorganism with a replicative and integrative plasmid comprising an autonomous replicating sequence, exogenous nucleotidic material, and a selection marker. The transformed cells are replicated to produce a number of generations of progeny cells. The process also involves selecting for cells which include the selection marker, and promoting the retention of the replicative and integrative plasmid in subsequent generations of the progeny cells to produce progeny cells having multiple integrated copies of the exogenous nucleotidic material. Optionally, the process further comprises: repeatedly replicating the progeny cells to produce a number of generations of progeny cells in the absence of selection for cells which include the selection marker, so as to promote the loss of the plasmid in subsequent generations of progeny cells; and recovering the cells each containing multiple copies of the exogenous nucleotidic material integrated into its endogenous nucleotidic material.

Selection markers may vary. For example, antibiotic resistance genes are often to be used as selection markers. The substrates need the cloned genes for their use can also be used as the selection markers for cloning the desired gene(s).

The resulting recombinant organism may include a large number of copies of the exogenous nucleotidic material integrated into endogenous nucleotidic material, for example, more than 10 copies. The resulting microorganism may also exhibit a fermentation activity that does not decrease after culture in non-selective medium for 20, 40, several hundred, or more generations.

The exogenous nucleotidic material may be integrated at reiterated DNA sequences. Such sites may be non-transcribed sites. The non-transcribed reiterated DNA sequences such as the 5S DNA The exogenous nucleotidic material may be fused to non-glucose-inhibited promoters and the yeast simultaneously ferments glucose and xylose to ethanol.

It should be noted that the invention is not necessarily limited to intentional recombinant methods known in the art.

Accidental formation of a microorganism having genes that code for glucoamylase expression and xylosic digestion may occur.

Culturing and Preserving Conditions

The following example sets forth general parameters for culturing and preserving all TEKK microorganism developed to date.

A. Avoid Keeping the Seed Culture on Slants or Plates

One should avoid keeping the seed culture on slants or plates. It should be kept in a 300 ml shaker flask at 4° C. The seed culture can be kept for 3 months at 4° C. Every 3 months, one or more flasks of fresh seed culture should be prepared as needed (following the procedure below for culturing the cells). The seed culture can be transferred and kept as described above even for years so long as the fermentation results remain the same. Nevertheless, from time to time (every six months), a new batch of cultures should be prepared for long-term storage at −70° C.

It is better not to spread the culture on plates to be stored as single colonies. Instead, it is recommended that the culture be maintained as liquid culture. When new seed cultures are made by transferring an aliquot of the existing culture to grow the new seed culture under the selected conditions, the more efficient cells for the intended purpose may be selected and enriched. As such, the culture should not only remain to be effective for the intended purpose and even become more effective for the intended purposes to give good fermentation performance.

B. Preparing Stock Culture for Long Term Preservation

To prepare stock culture for cryopreservation, pipet 0.9 ml freshly cultured seed culture and 0.9 ml 50% sterilized glycerol into each of 2.0 ml cryogenic vials. Mix the cell culture with the glycerol solution well and dip the tubes into a thick dry ice/ethanol bath. Store the tubes containing the frozen cultures in a −70° C. (or lower) freezer.

C. Culture Media

Two kinds of media are routinely used: YEPX or YEPD for culturing, maintaining, and long term preserving the glucose/xylose or C5/C6 co-fermenting yeast. YEPX is used for constructing, maintaining, and preserving the yeast that also contains the externally cloned glucoamylase gene. YEPX contains 1% yeast extract, 2% peptone, and 2% the selection marker xylose used for cloning and maintaining the glucoamylase gene to be used for culturing the seed culture and for long-term preservation of the culture at −70° C. YEPD contains 1% yeast extract, 2% peptone, and 2% glucose, and is used for pre-growing yeast for fermentation.

YEPX, or YEPD is essentially YEP plus 2% a specific sugar. YEP can be prepared in any clean flask so long as the size is appropriate for the final YEPD and/or YEPX needed. An appropriate volume of YEP is first measured and then transferred into the flask that will be used for culturing the cells. For example, if a 300 ml flask (preferably equipped with a side arm for use with a Klett colorimeter to follow cell growth) is to be used for cultivation of the cells either for seed culture or for fermentation, 100 ml of the YEP should be transferred into the flask. The flask is then plugged with either a cotton or foam plug and then sterilized in an autoclave at 121° C. for 20 minutes. Many such flasks can be prepared ahead of time, if they are needed frequently. The flasks can be kept on a shelf or in a cabinet at room temperature or in a refrigerator until they are used. However, the medium in the flask should be examined by lightly swirling it and inspecting it by eye to check for the growth of any contaminates before use. If the flask containing the sterilized YEP is used for culturing the seed culture, 4 ml of sterilized 50% xylose (50 g in 100 ml water) is added to the flask under sterilized conditions to make the final xylose concentration of the resulting YEPX close to 2%. If the flask containing 100 ml of sterilized YEP is used for fermentation, 4 ml of sterilized 50% glucose (prepared the same way as the 50% xylose) should be added under the same sterile conditions.

D. Culturing Temperature and Time

The cells should be cultured at 28-30° C. overnight in proper medium and at least for 16 hrs in a shaker at suitable rpm such as 200 rpm until the optical density is around 400 KU (Klett units) or higher (e.g., 22-26 $OD_{600}$).

E. Seed Culture Propagation

Several media may be used in seed culture propagation. In turn, the seed culture may be used to ferment glucose (or to co-fermenting glucose and xylose) to ethanol while producing glucoamylase. For example, to produce a seed culture that facilitates glucoamylase production, 2-4 ml of a yeast culture containing, e.g., TEKK or another suitable TEKK yeast, may be inoculated into a 300 ml flask containing 100 ml YEPG. The YEPG cultured seed culture may then be propagated in a medium containing corn mash provided by any corn ethanol producer. In turn, ethanol can then be produced from corn mash or starch treated with α-amylase or oligosaccharides. As described above, fermentation should be carried out the best at 28-32° C. As discussed below, an exemplary protocol is set forth below for fermenting corn mash.

F. Testing the Seed Culture

For testing the seed culture for TEKK or other glucose or xylose fermenting yeast that contains, for example, the natural and/or cloned glucoamylase gene actively producing glucoamylase, no special medium is needed, and the medium for culturing TEKK or for culturing other yeast or other microorganisms is sufficient. For culturing TEKK able to produce the natural yeast glucoamylase is 2-4 ml of the freshly prepared seed culture should be inoculated into a 300 ml flask containing 100 ml sterilized YEPD or YEPX and incubated in a 28-30° C. shaker until the density of the culture is over 400 KU.

Using standard methods for assaying (or analyzing) the enzyme activity, very little glucoamylase activity is typically found in the cultural medium itself. However, yeast such as TEKK that produces the natural glucoamylase have been observed to ferment feedstock such as corn mash that contains oligosaccharides obtained from treating starch with alpha-amylase to ethanol. This observation indicates that the enzymes (glucoamylase) produced by the yeast is not secreted into the cultural media, but that the enzymes can nevertheless help to degrade the oligosaccharides present in corn mash to glucose. In turn, glucose is fermented by the yeast to produce ethanol.

For fermenting corn mash to form lactic acid and ethanol by the glucose/xylose co-fermenting yeast such as TEKK-C5C6, the yeast cells are growing in corn ethanol producers' medium to more than 400-450 KU or OD 22-26. The cells are then centrifuged and transferred to flasks containing enough corn mash sufficient for producing more than 16% ethanol. How much ethanol the yeast can produce in 60-72 hours that will be a direct measure on how much glucoamylase the yeast can provide. It turns out the TEKK yeast can produce at least 14-16% g/l ethanol within 12 to 72 hours from the corn mash produced by different companies that are using corn as the feedstock to produce ethanol. For using the TEKK yeast to ferment corn mesh, the flask should be covered with three layers of Saran wrap (or equivalent strong plastic film) over the plug. The saran wrap should fully encompass the plug and is tightly bound to the flask with three to four strong rubber bends to limit the air flowing into the flask. This ensures that the contents within the flask are at least under micro-aerobic conditions, if not totally anaerobic. The flask is then incubated in the shaker for fermentation to proceed. 1 ml samples are taken from the flask under sterile conditions and transferred to a 1.5 ml Eppendorf tube at 0, 3, 6, 12, 24, 36, 48 hrs or longer, but not more than 72 hours. The cells in the sample tubes will be spun down and the supernatant in each sample tube will be transferred into another properly labeled Eppendorf tube (do not need to transfer every drop of the supernatant but make sure no cells are transferred). These tubes are then kept in a freezer until the samples can be analyzed by HPLC. The HPLC is carried out as described by the conditions provided.

General Comments

The TEKK strains of yeasts are stable and do not require special handling. The only consideration is that the seed cultural should be cultured under sterilized conditions and the medium should be properly prepared and sterilized as instructed.

Any container used with the TEKK strains of yeast described herein, including the small Eppendorf tubes, is better sterilized before being discarded or washed by any procedure to prevent the culture to be released and obtained by those not entitled to have such a yeast.

It is strongly recommended that any lab using recombinant yeast for glucosic and/or xylosic fermentation should purchase a Klett colorimeter and a couple dozens 300 ml flasks with a side arm. They make cell density measurements easier and more accurate, less time consuming, and less possibility to introduce contaminates into the culture.

Examples of Enzyme Production

Numerous organic compounds were produced separately by various strains of TEKK yeast. Here, for example, the glucose-xylose co-fermenting cells with cellulase activities are also able to ferment arabinose sugar.

As a first example, TEKK-β-glucosidase was produced. Beta glucosidase gene from *S. fibulgera* was cloned into a high copy 2u yeast plasmid. The resulting plasmid was cloned into TEKK strain. Right colony was selected on hygromycin plate. Cells were grown in YPED medium with hygromycin. Cells were transferred to YPEX medium with hygromycin. Enzyme activity was measured using p nitrophenyl glucopyranoside.

The beta glucosidase gene was cloned into integration plasmid. The arabinose metabolizing gene was also inserted into the integration plasmid. The arabinose gene was inserted because it could use the arabinose sugar present in the biomass and also as a selection marker. The TEKK strain was cloned with the integration plasmid. The colonies were selected on hygromycin plate. The cells were grown in YPED medium with hygromycin. Cells were transferred to YPEX medium with hygromycin. Cells were grown in the YPEX+hygromycin liquid medium for several generations. Glucosidase activity was measured in the liquid culture.

To test that the presence of glucosidase and arabinose gene did not affect on the glucose-xylose fermentation, a fermentation study was performed in the presence of glucose and xylose. Both sugars were efficiently converted into ethanol when TEKK-glucosidase strain was used.

As another example, TEKK-Endocellulase was produced. The endocellulase gene was from *T. reesei*. The codons were optimized for yeast expression. The cDNA was synthesized. The endocellulase cDNA was inserted first into high copy 2u plasmid. The TEKK was cloned with the plasmid containing endocellulase gene.

The colonies were isolated on hygromycin plate. Cells were grown in YPED medium with hygromycin. Cells were transferred to YPEX medium with hygromycin. The activity of endocellulase was measured in liquid culture using carboxy methyl cellulose. The sugar was detected either GOD kit from Sigma or Dinitro salicylic acid. The endocellulase gene was inserted into integration plasmid which also carried arabinose gene. The TEKK strain was transformed with the integration plasmid. Colonies were selected on hygromycin plate. Cells were grown in YPED medium with hygromycin.

As a further example, TEKK-Exocellulase was produced. The exocellulase gene was from *T. reesei*. The codons were optimized for yeast expression. The cDNA was synthesized. The exocellulase cDNA was inserted first into high copy 2u plasmid. The TEKK was cloned with the plasmid containing endocellulase gene.

The colonies were isolated on hygromycin plate. Cells were grown in YPED medium with hygromycin. Cells were transferred to YPEX medium with hygromycin. The activity of exocellulase was measured in liquid culture using phosphoric acid swollen cellulose. The sugar was detected either GOD kit from Sigma or Dinitro salicylic acid.

The endocellulase gene was inserted into integration plasmid which also carried arabinose gene The TEKK strain was transformed with the integration plasmid. Colonies were selected on hygromycin plate. The activity of endocellulase was measured in liquid culture using carboxy methy cellulose.

Figure 1:
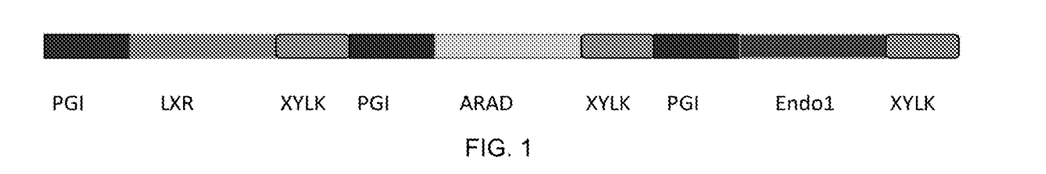
FIG. 1 depicts a schematic diagram of cellulase and arabinose metabolizing genes. The figure shown below is representing the endocellulase gene. In beta glucosidase and exocellulase constructs, the corresponding genes are placed in endocellulase gene.

FIG. 1 shows the schematic diagram of cellulase and arabinose metabolizing genes. The figure shown below is representing the endocellulase gene. In beta glucosidase and exocellulase construct, the corresponding genes are placed in endocellulase gene. The following serves as a key to understanding FIG. 1

PGI—phosphoglucose Isomerase Promoter from *Saccharomyces cerevisiae*

XYLK—xylulose kinase terminator from *Saccharomyces cerevisiae*

LXR—L-xylulose reductase coding sequence from *A. monospora*

ARAD—arabitol dehydrogenase coding sequence from *T. reesei*

Endo1—endocellulase *T. reesei*

For betaglucosidase (*S. fibulgera*) or exocellulase (*T. reesei*), the gene was placed in place of Endo1.

Glucose and xylose cofermentation by the beta glucosidase producing TEKK-stains. The figure shows that after including the beta glucosidase gene, the fermentation ability of the strain is not affected.

TEKK-LAC and Improved Lactic Acid Production

In general, baseline TEKK-LAC and variants thereof, i.e., *Saccharomyces cerevisiae* and subspecies thereof, can be used effectively for production of lactic acid from glucose, xylose, mixture glucose/xylose, and other sugars present in lignocellulosic hydrolysates of biomass. Prior to and/or concurrent with the filing of the subject patent application, a culture of TEKK-LAC yeast and/or variants thereof have been submitted to a U.S. depository under the International Depositary Authority (IDA) as established under the Budapest Treaty on the International Recognition of the Deposit of Microorganisms for the Purposes of Patent Procedure. As far as applicant is aware, the deposit culture is genetically and/or epigenetically distinct from previously known microorganism cultures, as discussed below.

Figure 2:
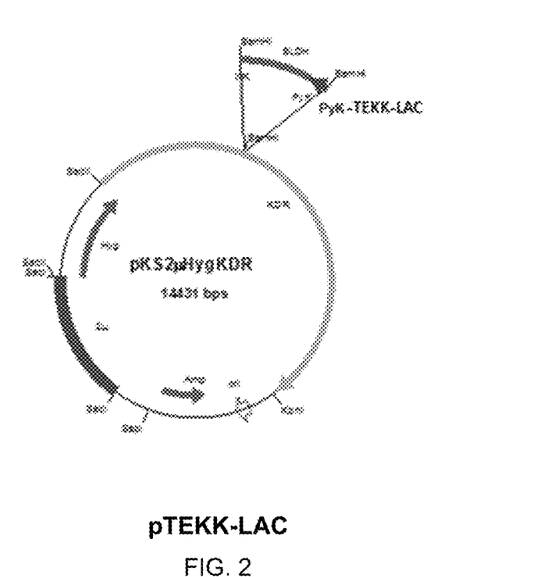
FIGS. 2-3 are drawings associated with exemplary TEKK-LAC strains of microorganisms, including, for example, TEKK-LAC-baseline strains.

Originally, TEKK-LAC was produced using plasmids pTEKK-LAC (a derivate of p424A(LNH-ST), see, e.g., FIG.

2, pYKDR-TEKK-LAC is a high copy number plasmid containing the cloned xylose reductase gene, the xylitol dehydrogenase gene, xylulokinase gene (KDR) and the TEKK-LAC gene (pYKDR-TEKK-LAC is a derivative of p(4242A(LNH-ST)).

Integration multiple copies of bacterial lactate dehydrogenase (TEKK-LAC) into Saccharomyces cerevisiae 424A (LNH-ST) chromosome was carried out using the integration plasmid, pTEKK-LAC. The resulting yeast, Saccharomyces cerevisiae TEKK-LAC, was used to characterizing lactic acid production as well as the development new and improved strains for lactic acid production.

Construction of ethanol—mutant of Saccharomyces cerevisiae TEKK-LAC may involve creation of the Saccharomyces cerevisiae TEKK-LAC EtOH—through disruption of genes significant for ethanol production, such as the pyruvate decarboxylase genes.

The Saccharomyces cerevisiae strain converting xylose, glucose and mixture glucose/xylose to lactic acid was constructed by transformation of Saccharomyces cerevisiae TEKK-LAC with pYKDR-TEKK-LAC.

Fermentation was performed in a 300 ml baffled Erlenmeyer flask. The yeast was pre-grown in 100 ml YEPE (2% ethanol) or YEPD (2% glucose) until cell density reached 400-450 Klett unit (8-9 g dry wt/L). At this point, glucose or xylose or mixture glucose and xylose were added to each flask.

Figure 4:
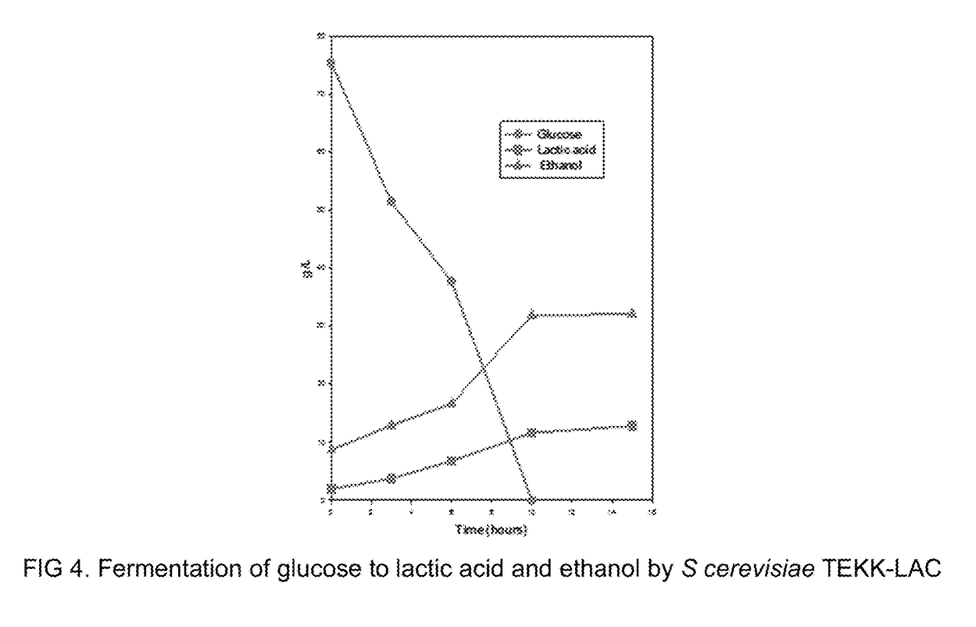
FIGS. 4-9 are graphs depicting the experimental performance of exemplary TEKK-LAC strains of microorganisms, including, for example, TEKK-LAC-baseline strains.
Figure 5:
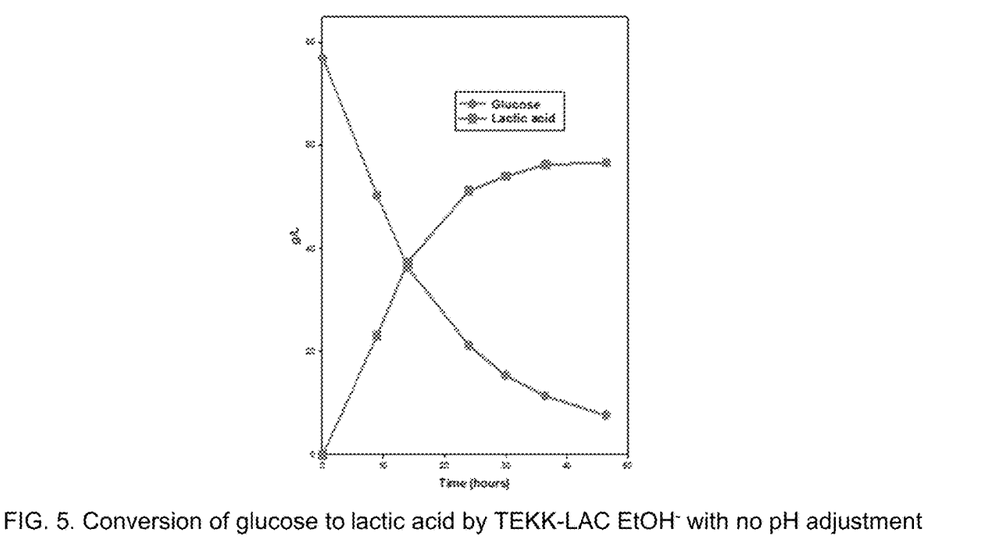
Figure 6:
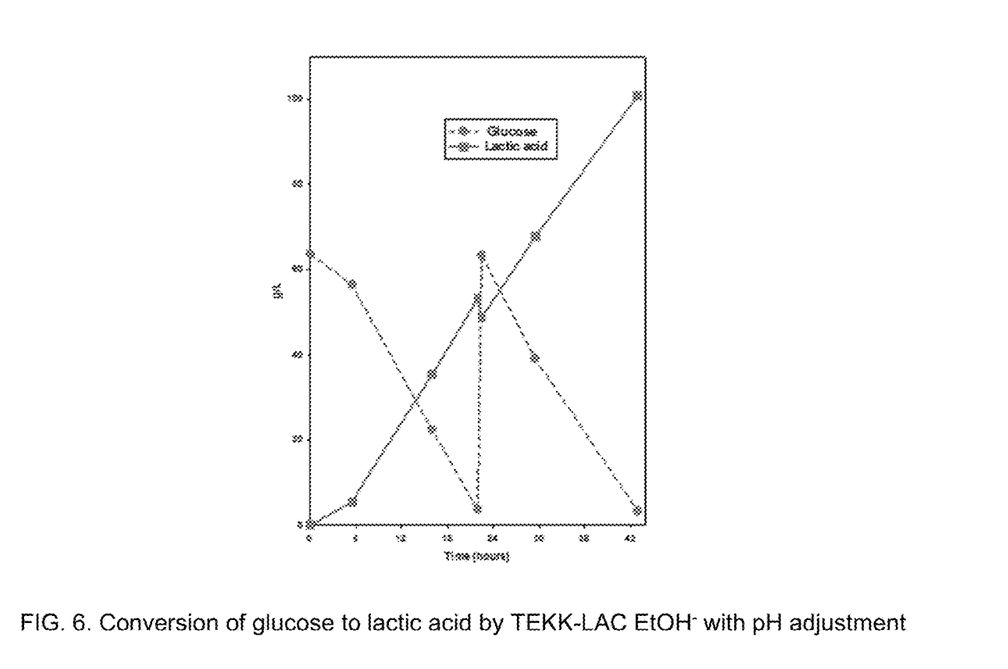

Thus, Saccharomyces cerevisiae and variants thereof can be used effectively for production of lactic acid from glucose, xylose, mixture glucose/xylose, and sugars present in lignocellulosic hydrolysates. Recombinant Saccharomyces cerevisiae TEKK-LAC carrying permanently integrated multiple copies of bacterial lactate dehydrogenase to its chromosomes was able to produce lactic acid however it also simultaneously produced ethanol in approximate a 1:2 ratio (FIG. 4). The co-production of ethanol can be disabled by abolishing the cell's ability to produce certain enzymes significant for ethanol production. Genetically modified Saccharomyces cerevisiae TEKK-LAC EtOH⁻ was able to produced lactic acid as sole product (FIG. 5). This demonstrates the capability of genetically modified yeast to produce lactic acid to relatively high concentration (≈60 g/L) with good yield (≈81.6%) without the need of adjusting/controlling pH (FIG. 5). When pH was controlled using $CaCO_3$ during fermentation (pH≈4.5-5) TEKK metabolically modified yeast were able to produce lactic acid up to 100 g/L in a much shorter time (FIG. 6) with yield of 84%.

Renewable resources such as starch and cellulosic biomass (corn stover, bagasse, rice and wheat straw, wood, municipal and industrial paper wastes etc.) can be use as substrates for production of lactic acid. It would be great advantage in lactic acid production if lactic acid producing yeast would be able to convert as many sugars in cellulosic biomass hydrolysates as possible. A second major sugar present in cellulosic biomass hydrolysates is xylose. However, naturally occurring Saccharomyces cerevisiae was found to be unable to ferment xylose and also unable to use the sugar for growth nevertheless TEKK genetically modified Saccharomyces cerevisiae is capable of both. In addition, TEKK xylose fermenting Saccharomyces cerevisiae not only can effectively co-ferment both glucose and xylose, but also can co-ferment other sugars present in cellulosic biomass, such as mannose, and galactose.

Figure 3:
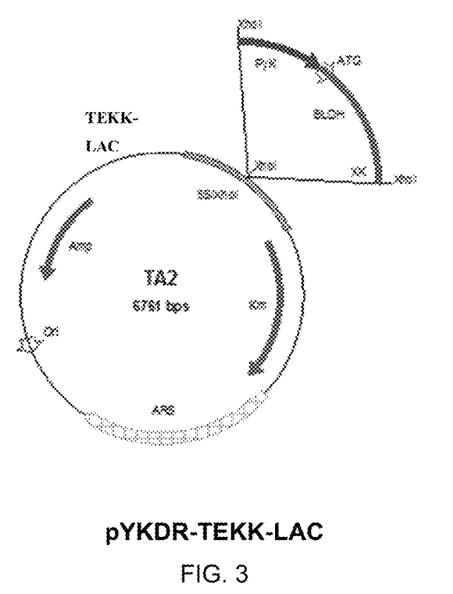
Figure 7:
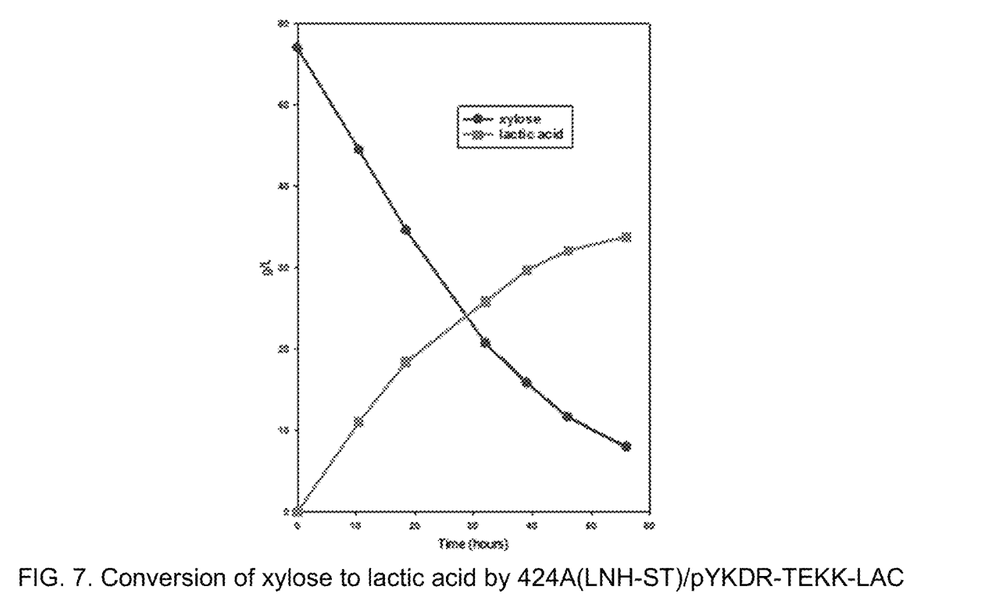
Figure 8:
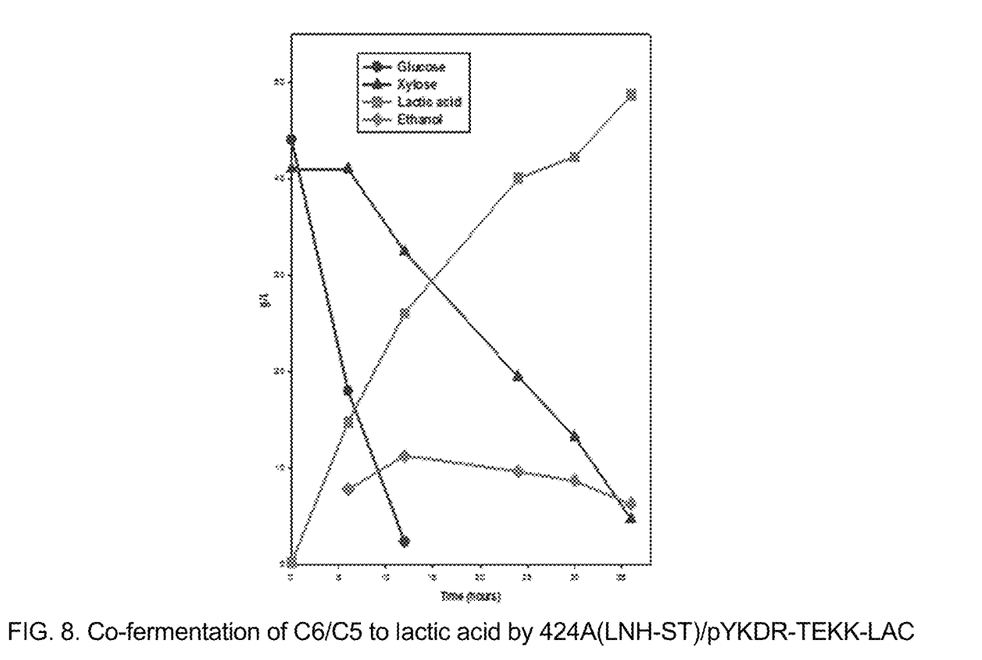

To test the possibility of using sugars from cellulosic biomass to produce lactic acid by yeast, bacterial LDH as cloned into pKS2μHygKDR plasmid (this plasmid harbors all the necessary genes for xylose utilization in yeast) and the resulting plasmid pYKDR-TEKK-LAC (FIG. 3) was transformed into Saccharomyces cerevisiae 424A(LNH-ST). The resulting strain Saccharomyces cerevisiae 424A (LNH-ST)/pYKDR-TEKK-LAC was able to convert xylose to lactic acid (FIG. 7). Furthermore, surprisingly no ethanol co-product was detected (FIG. 7). This indicates that xylose is a suitable substrate for TEKK engineered yeast to produce lactic acid. As mentioned above, TEKK xylose metabolizing strains is also capable of co-fermentation of both glucose and xylose. When the same genetically modified strain Saccharomyces cerevisiae 424A(LNH-ST)/pYKDR-TEKK-LAC was used to co-ferment a mixture of glucose and xylose, the levels of ethanol produced are lower than when only glucose is converted to lactic acid (FIGS. 8 and 4).

Figure 9:
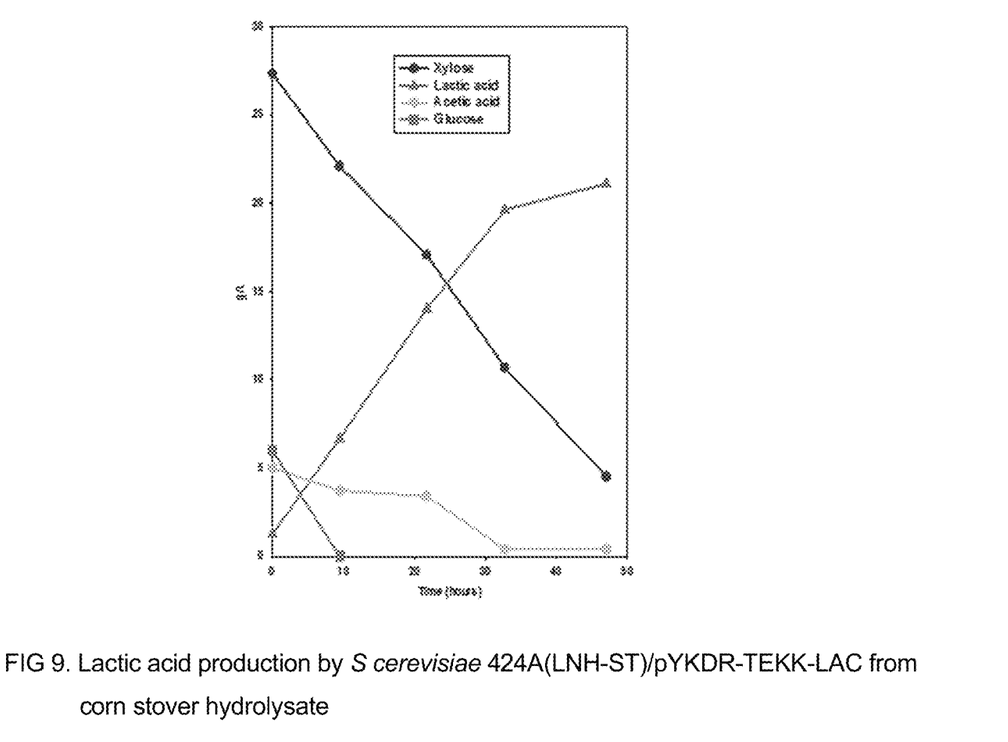

Cellulosic biomass can be converted to fermentable sugars by a hydrolysis process. However, lignocellulosic hydrolysates are not merely sugar solutions; they also contain a large number of other compounds, even though in small quantities. However, many of those minor components might inhibit the performance of the fermenting microorganisms. Thus, whether the recombinant yeast is able to tolerate the inhibitors present in the hydrolysates is also an important factor. To assess the prospect for lactic acid production from xylose rich hydrolysates, xylose fermenting-lactic acid producing strain Saccharomyces cerevisiae 424A(LNH-ST)/pYKDR-TEKK-LAC was used to ferment such hydrolysate. The results of this study indicate (FIG. 9) that TEKK metabolically modified yeast should be able to produce lactic acid from glucose/xylose rich lignocellulosic hydrolysates.

Thus, a number of nonobvious aspects of the invention will be apparent upon inspection by a person having ordinary skill in the art in view of the disclosure above and otherwise contained herein. For example, the experimental data shown in FIGS. 4-9 depict improvements in lactic acid generation to a nonobvious degree relative to known yeasts, e.g., relative to those discussed in Ishida et al., "Efficient Production of L-Lactic Acid by Metabolically Engineered Saccharomyces cerevisiae with a Genome-Integrated L-Lactate Dehydrogenase Gene," Appl and Environ Microbiol (2005) 71(4): 1964:190, in an industrial scale associated with domesticated plants available on an acreage scale.

Variations on the invention will be apparent to persons of ordinary skill in the art. For example, while the nucleotic material associated with the invention may be located in a single species of microorganism, the invention may include more than one species. In such a case, microorganisms of differing species may exhibit similar culturing requirements so that they may be used to co-ferment glucosic and xylosic materials simultaneously. In addition, it is envisioned that the invention may employ a particular batch process, continuous process, or combination thereof to produce an organic compound of interest in purities of interest, i.e., in the absence of impurities of appropriate proportional ranges. Similarly, stirring rates may be determined to avoid excessive fluidic shearing forces that may compromise the execution of the invention.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected. Furthermore, any numerical range set forth herein is to be interpreted in a manner such so as all numbers within the range is specifically called out. For example, recitation of a range from 1 to 2 includes recitations of 1, 2, 1.5, 1.1, 1.2, 1.3, 1.4, 1.5, 1.6, 1.7, 1.8, 1.9, 1.01, 1.001, 1001, 1.25, 1.75, etc.

In the claims below, the subject matter recited therein may be amended and/or interpreted so as exclude certain subject matter discussed herein to ensure that any claims that may ultimately be granted and be enforced in a manner such that they are valid according to all relevant sections of relevant patent laws, e.g., 35 U.S.C. sections 101, 102, 103, and/or 112.

All patents and publications referenced herein are incorporated by reference to the fullest extent practicable not inconsistent with the above disclosure. All claims below are to be construed as having the broadest, reasonable, and valid scope in all fora, e.g., all US courts and administrative agencies, all international courts and administrative agencies, and all other non-US national courts and administrative agencies.

What is claimed is:

1. A method for producing a desired biochemical in an industrial scale volume, comprising the steps of:
    (a) putting together in a container of industrial-scale volume biomass of an industrial-scale volume,
    water, and
    a TEKK-LAC yeast that enzymatically breaks down glucosidic and xylosic material of the biomass; and
    (b) bringing the container to a temperature suitable for the TEKK-LAC or variant yeast to produce the desired biochemical in an industrial-scale volume,
    wherein the desired biochemical comprises lactic acid.

2. The method of claim 1, further comprising (c), isolating the desired biochemical from a byproduct.

3. The method of claim 1, wherein (c) involves a distillation step.

4. The method of claim 1, wherein (c) involves a filtration step.

5. The method of claim 1, wherein residue from the method is fed to an animal and/or human.

6. The method of claim 1, wherein the TEKK-LAC yeast also produces β-glucosidase.

7. The method of claim 1, wherein the desired biochemical further comprises TEKK-endocellulase, TEKK-exocellulase, and/or TEKK-β-glucosidase, and/or a functionally active variant thereof, that digests C5 and C6 sugars.

8. The method of claim 1, comprising a live TEKK-LAC yeast culture that produces lactic acid by digesting a C5 compound and a C6 compound via lactose production through activity of integrated multiple copies of bacterial lactate dehydrogenase within the TEKK-LAC yeast culture.

9. The method of claim 8, in a container of industrial-scale volume of at least about 1 gallon.

10. The method of claim 9, wherein the container of industrial-scale volume is a reaction tank having a capacity of at least about 1000 gallons.

11. The method of claim 8, comprising a domesticated plant available in an acreage scale.

12. The method of claim 8, comprising corn or a constituent thereof.

13. The method of claim 8, comprising corn stover or a constituent thereof.

14. The method of claim 8, wherein the culture of TEKK-LAC yeast efficiently produces lactic acid from at least a C5 carbohydrate or a polymeric version thereof relative to nonbioengineered culture of the same yeast.

15. The method of claim 14, wherein the TEKK-LAC yeast is effective to produce lactic acid in a nonnegligible quantity with nonnegligible scale of higher yield, efficiency, and/or purity relative to a nonbioengineered culture of the same yeast.

16. The method of claim 15, wherein the TEKK-LAC yeast is hardened for lactic acid production.

* * * * *